(12) United States Patent
Ku

(10) Patent No.: US 7,747,671 B2
(45) Date of Patent: Jun. 29, 2010

(54) DATA TRANSMISSION SYSTEM FOR LINKING MULTIPLE EXERCISE FACILITIES

(75) Inventor: Tse-Fen Ku, Taichung (TW)

(73) Assignee: King I Tech Corporation, Taichung (TW)

( * ) Notice: Subject to any disclaimer, the term of this patent is extended or adjusted under 35 U.S.C. 154(b) by 1936 days.

(21) Appl. No.: 10/645,597

(22) Filed: Aug. 22, 2003

(65) Prior Publication Data

US 2005/0044210 A1    Feb. 24, 2005

(51) Int. Cl.
*G06F 15/16* (2006.01)
(52) U.S. Cl. .......................... 709/200; 709/224; 482/8; 482/93
(58) Field of Classification Search ................. 709/200, 709/224; 482/8, 54
See application file for complete search history.

(56) References Cited

U.S. PATENT DOCUMENTS

| | | | | |
|---|---|---|---|---|
| 5,598,849 | A * | 2/1997 | Browne | 600/520 |
| 6,224,519 | B1 * | 5/2001 | Doolittle | 482/98 |
| 6,231,481 | B1 * | 5/2001 | Brock | 482/8 |
| 6,450,922 | B1 * | 9/2002 | Henderson et al. | 482/8 |
| 6,601,016 | B1 * | 7/2003 | Brown et al. | 702/182 |
| 6,702,719 | B1 * | 3/2004 | Brown et al. | 482/8 |
| 6,746,371 | B1 * | 6/2004 | Brown et al. | 482/8 |
| 6,921,351 | B1 * | 7/2005 | Hickman et al. | 482/8 |
| 7,488,277 | B1 * | 2/2009 | Knapp | 482/104 |
| 2001/0041647 | A1 * | 11/2001 | Itoh et al. | 482/9 |
| 2002/0022551 | A1 * | 2/2002 | Watterson et al. | 482/8 |
| 2002/0042328 | A1 * | 4/2002 | Yoo | 482/8 |
| 2002/0045519 | A1 * | 4/2002 | Watterson et al. | 482/54 |
| 2002/0082142 | A1 * | 6/2002 | Cannon et al. | 482/1 |
| 2004/0092367 | A1 * | 5/2004 | Corbalis et al. | 482/54 |
| 2004/0171464 | A1 * | 9/2004 | Ashby et al. | 482/54 |
| 2004/0198555 | A1 * | 10/2004 | Anderson et al. | 482/8 |
| 2005/0071197 | A1 * | 3/2005 | Goldberg | 705/2 |
| 2005/0075214 | A1 * | 4/2005 | Brown et al. | 482/8 |
| 2005/0233861 | A1 * | 10/2005 | Hickman et al. | 482/8 |
| 2005/0272561 | A1 * | 12/2005 | Cammerata | 482/8 |
| 2006/0063644 | A1 * | 3/2006 | Yang | 482/4 |
| 2007/0265138 | A1 * | 11/2007 | Ashby | 482/8 |
| 2008/0171922 | A1 * | 7/2008 | Teller et al. | 600/301 |

* cited by examiner

*Primary Examiner*—Hassan Phillips
*Assistant Examiner*—Anthony Mejia
(74) *Attorney, Agent, or Firm*—Muncy, Geissler, Olds, & Lowe, PLLC

(57) ABSTRACT

A data transmission system for linking multiple exercise facilities includes at least one exercise facility which has a measurement device mounted thereon for capturing data or detecting, and a transmission circuit which has one end connecting to the exercise facility and other end connecting to a microprocessor. The transmission circuit connects the exercise facility and the microprocessor to form a transmission system.

2 Claims, 5 Drawing Sheets

DATA TRANSMISSION SYSTEM FOR LINKING MULTIPLE EXERCISE FACILITIES

FIELD OF THE INVENTION

The present invention relates to a data transmission system and particularly to a data transmission system for linking a plurality of exercise facilities.

BACKGROUND OF THE INVENTION

In recent years medical researches indicate that regular exercise can bring a lot of benefits to people and improve their health regardless the age of people. Exercise also can reduce the risk of inflicting chronic diseases, prevent coronary artery heart attack, help people to lose weight and keep people slim physically.

In general people who do exercise persistently have a lower death rate than those who don't. Ideal exercise enables people to fully enjoy the pleasure of exercise and improve functional efficiency of the organs in the body, and enhance resistance against diseases.

A research report indicates that healthy people have a lower death rate by cancers. It concludes that regular exercise and the possibility of inflicting cancers are related.

In view of these findings, modern people have a growing awareness of the importance of exercise. Many people participate outdoor exercises in holidays. In addition, in recent years body building is highly fashionable and many gymnasiums have beet setup. More and more people go to the gyms to do exercise after work or school.

Gym offers an advantage by gathering a wide variety of exercise facilities and can help people to focus on various parts of muscle of body to do training, such as running mills, stepping machines, and weight lifting machines, and the like. It can gather people together and save people's time. However most people who go to the gym to do exercise often neglect the importance of regular exercise and do not keep records. Everyone has a different time limit for continuous running and a different capability for weight lifting. While the coaches in the gym may pay attention to the condition of people during exercises, they generally focus on whether people are using the exercise facilities properly. They cannot spend a lot of time to care the details about the physical difference of each individual user, such as running time and speed, lifting weight, etc. Many people do not know their physical limitation and capability. Hence exercise injury resulting from over exercise happens frequently.

Therefore there is a need to keep detailed records and long term tracking for people to do exercise in the gym. By keeping the data and records, not only the performance of exercise is readily available, analysis may be made based on these data to consult health advisers, and suitable running time and lifting weight may be obtained to help users to achieve the objects of exercise and healthcare.

SUMMARY OF THE INVENTION

Therefore the primary object of the invention is to resolve the aforesaid disadvantages and to overcome the drawbacks in the prior art. The invention provides a data transmission system for linking multiple exercise facilities. Data captured from various exercise facilities are transmitted to a required interface such as a microprocessor or a storage device. Based on the data suitable reference values may be processed and obtained for each individual user.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
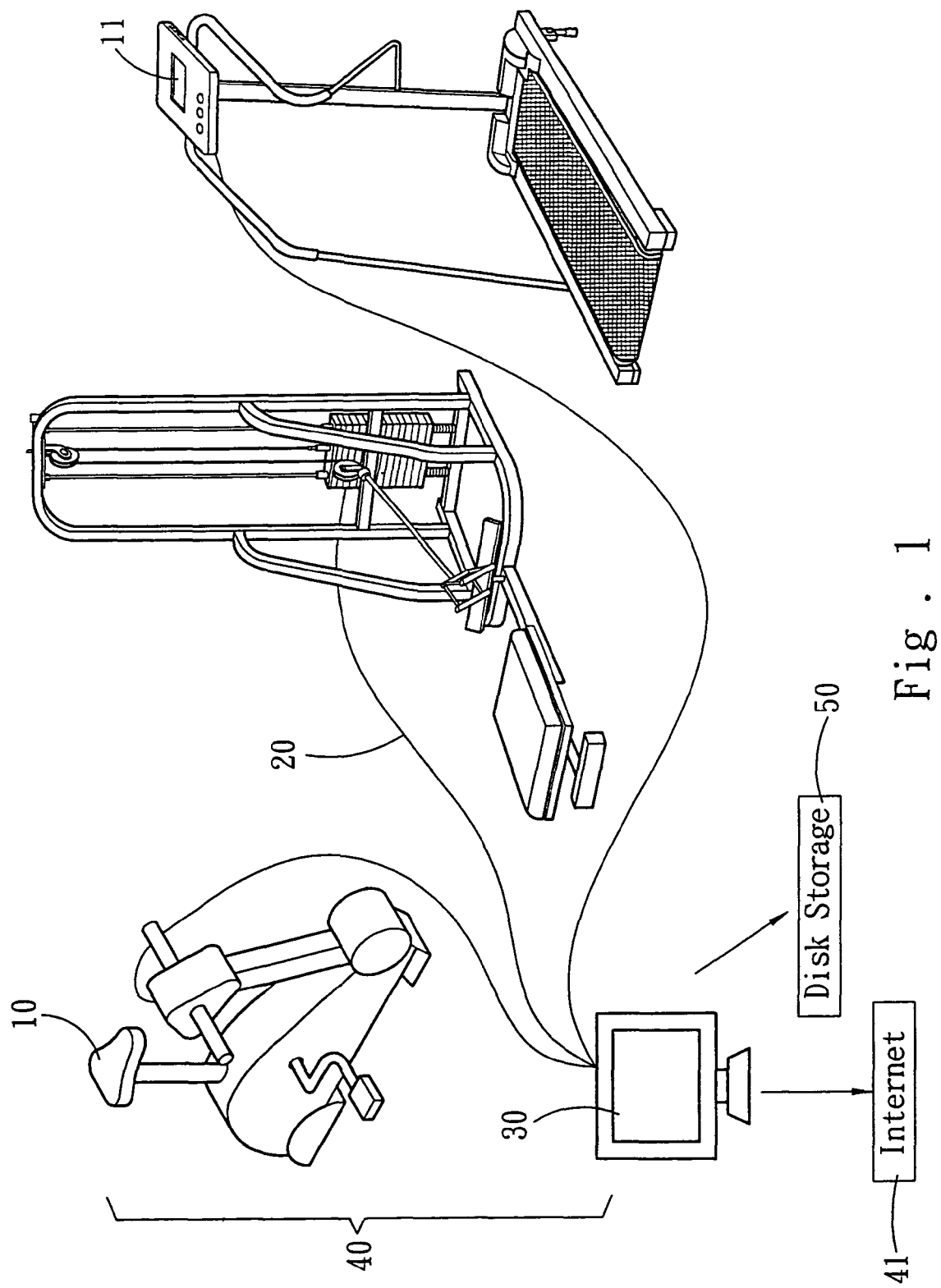
FIG. 1 is a schematic diagram of a preferred embodiment of the data transmission system of the present invention.

Please refer to FIG. 1 for an embodiment of the invention.

The invention includes one or more exercise facility 10 (such as stepping machine, running mill, weight lifting machine). Each exercise facility 10 provides different type of exercise functions. And each exercise facility 10 has a measurement device 11 for storing and retrieving data. For instance, the stepping machine and running mill have the measurement device 11 mounting on the handle to record and store data of users after the exercise is finished (such as running speed, distance, time, resistance, and user's heart beat value and blood pressure value). For the weight lifting machine, the measurement device may be located on the weights to record and store data of users after the exercise is finished (such as lifting times and pounds), and users' heart beat value and calorie consumption value; and a transmission circuit 20 which has one end connecting to the measurement device 11 of various exercise facility 10 and other end connecting to a microprocessor 30.

With the transmission circuit 20 linking between various exercise facility 10 and the microprocessor 30, a data transmission system 40 is formed which can achieve the following functions:

The measurement device 11 on the exercise facility 10 can capture data of the user after exercise (such as running speed, distance, time, resistance, and user's heart beat value and blood pressure value, or lifting times and pounds). The captured data are transmitted to the microprocessor 30 through the transmission circuit 20. The microprocessor 30 has processing programs resided therein to process the data and output reference values suitable to the physical conditions of each user (processing of the microprocessor 30 forms no part of the invention, thus details are omitted).

Figure 2:
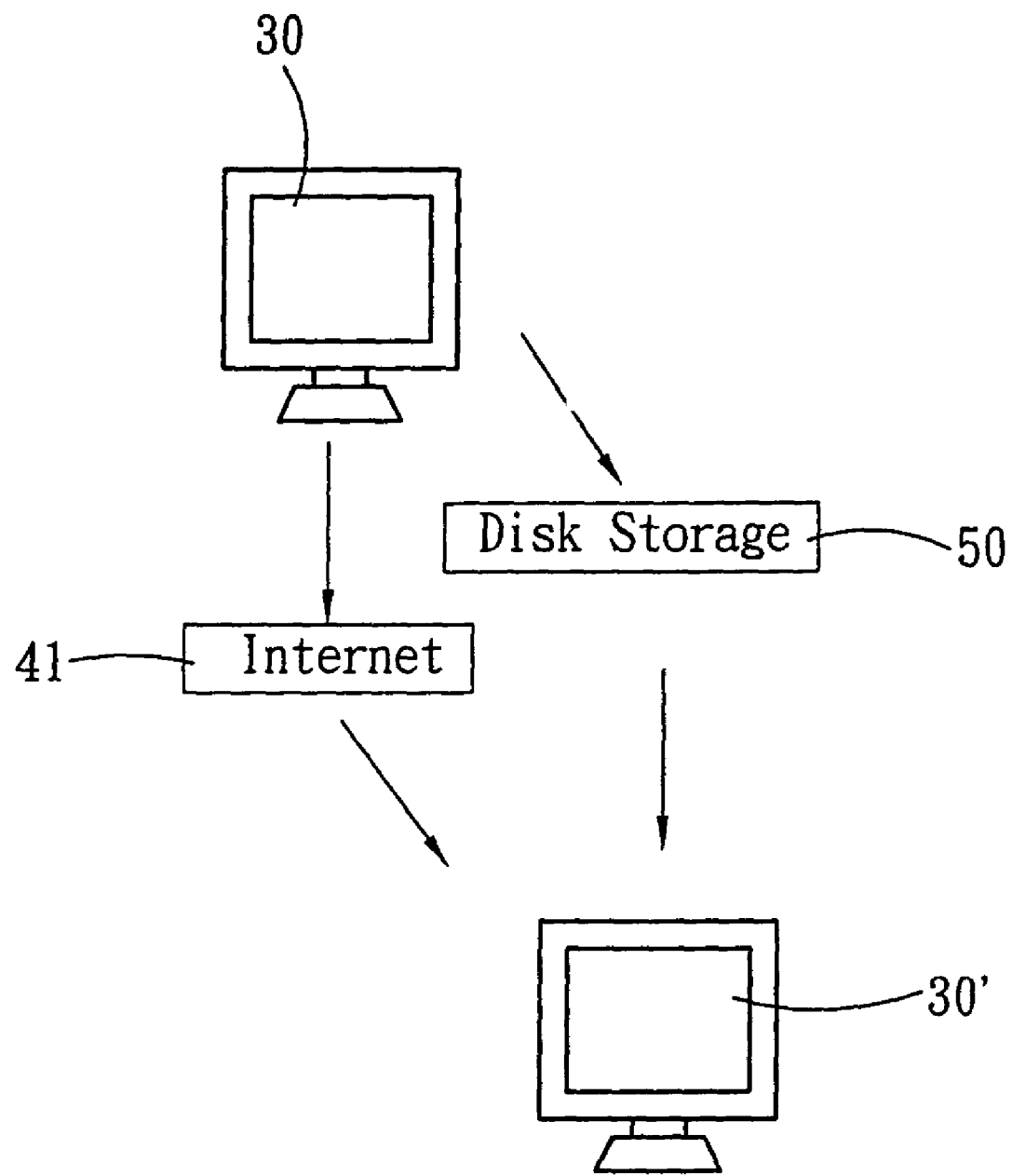
FIG. 2 is a schematic view of another data transmission system of the present invention with a microprocessor.

Refer to FIG. 2 for another transmission method of the invention. Aside from using a single microprocessor 30 to process data and output reference values suitable to the physical conditions of individual user, data may also be transmitted through the Internet 41 or a disk storage 50 to another microprocessor 30' (such as a health consulting center).

Figure 3:
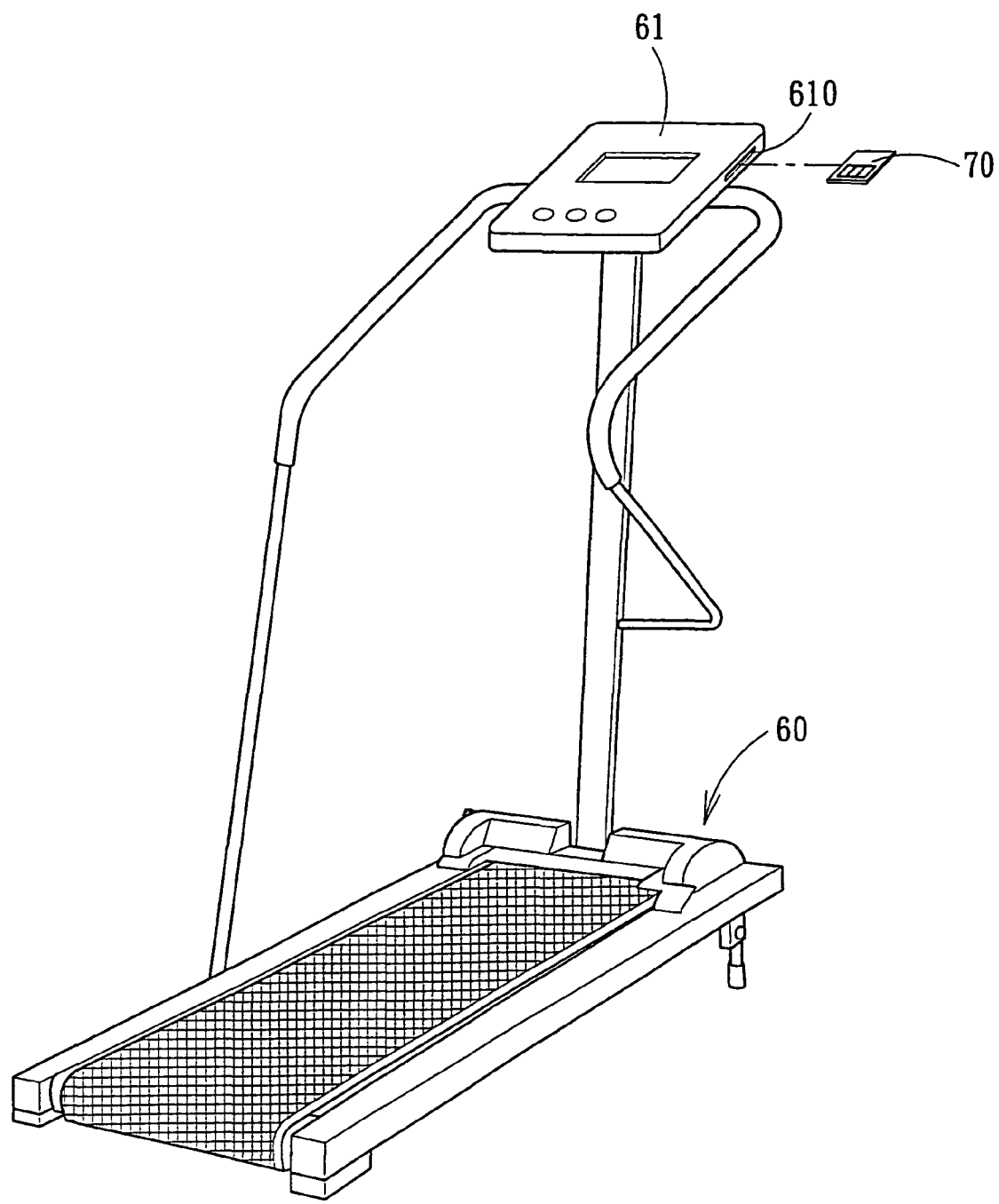
FIG. 3 is a schematic view of another preferred embodiment of the data transmission system of the present invention.

Refer to FIG. 3 for another preferred embodiment of the data transmission system of the invention.

The invention includes one or more exercise facility 60 (such as stepping machine, running mill, weight lifting machine). Each exercise facility 60 has a data reader 61 (such as a display instrument of a data storage mounted on the handle of the stepping machine and the running mill, a detection element located on the weights of the weight lifting machine). The data reader 61 can record users' data after the exercise is finished (such as running speed, distance, time, resistance, and user's heart beat value and blood pressure value, or lifting times and pounds). The data reader 61 has a slot 610; and a storage device 70 housed in the slot 610 of the data reader 61 to read the data stored in the data reader 61.

Figure 4:
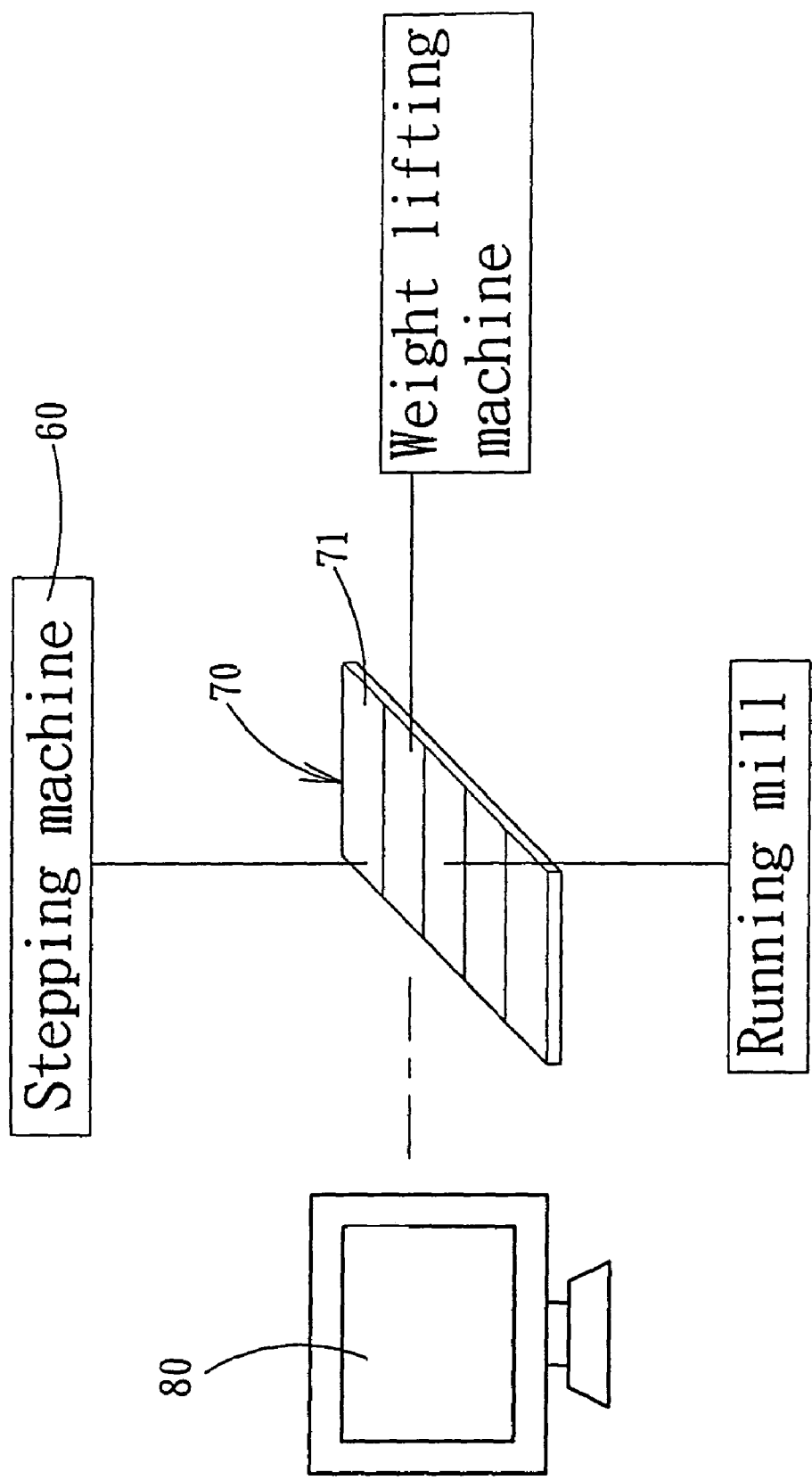
FIG. 4 is a schematic view of the invention showing a memory zone layout of the storage device.

Refer to FIG. 4 for the buffer layout of the memory zone of the storage device.

As shown in the drawing, the storage device 70 has at least one preset memory buffer 71. Each memory buffer 71 has different storage segments formed according to the properties of different exercise facility 60 (such as a speed buffer, distance buffer, time buffer, lifting time buffer and pound buffer, etc.)

Based on the second embodiment, the data reader 61 of each exercise facility 60 has a slot 610 to house a storage device 70 which may store users' data after exercise to enable a microprocessor 80 to access. The microprocessor 80 has processing programs resided therein to process the data and output suitable reference values according to the physical conditions of each individual user.

Figure 5:
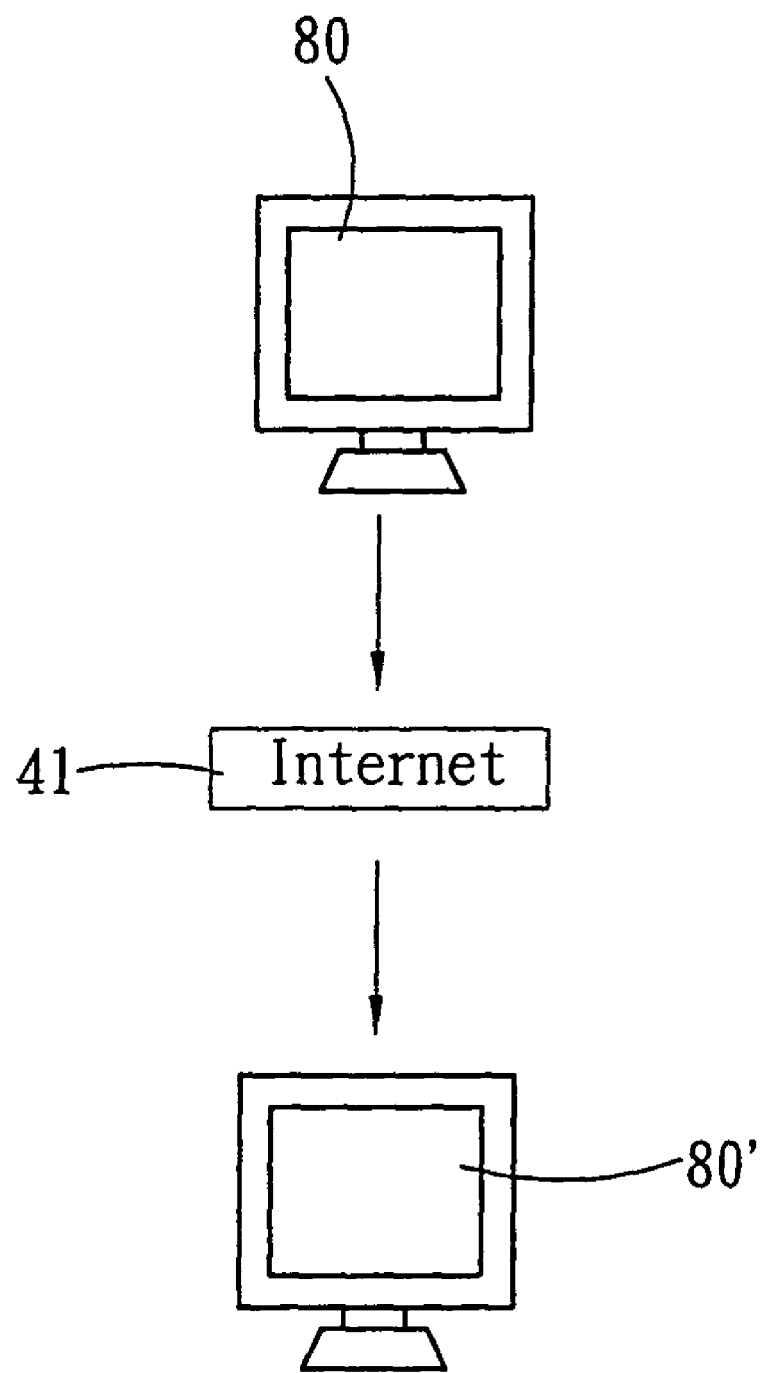
FIG. 5 is a schematic view of present invention showing yet another type of data transmission system including a microprocessor.

Refer to FIG. 5 for another type of data transmission system that includes a microprocessor. The microprocessor 80, besides processing in a standalone fashion, can also transmit exercise data through Internet 41 to another microprocessor 80' (such as a health consulting center).

By means of the first and second embodiments set forth above, the invention provides a data transmission system 40 and a data reader 61 linking to multiple exercise facilities 10 and 60. The data transmission system 40 and the data reader 61 are connected to the exercise facilities 10 and 60 to record data of every user after exercise. The data may be transmitted through a transmission circuit 20 to standalone microprocessors 30' and 80' or health consulting center. Then the microprocessors 30' and 80' or health consulting center can process the data and provide suitable reference values according to the physical conditions of each individual user.

Through the invention, the detailed data of every user doing exercises in the gym every time may be recorded and tracked on a long term basis. Not only the result and performance of exercise are readily available, the data can also be transferred to health consultants for analysis to workout a suitable program for each user such as suitable running time and lifting weight to effectively achieve the objects of exercise and healthcare.

What is claimed is:

1. A data transmission system for linking multiple exercise facilities, comprising:
   at least one weight lifting exercise facility which has a detection element on a weight, as a data reader for reading user data after an exercise is finished including a slot; and
   a storage device housed in the slot of the data reader for reading data stored in the data reader;
   a microprocessor connected to said storage device for processing data and outputting reference values of users according to physical conditions of each individual user;
   wherein the storage device has at least one preset memory buffer on the weight lifting facility which forms storage segments according to properties of the weight lifting exercise facility.

2. The data transmission system of claim 1, wherein the properties of the weight lifting exercise facility include at least one of lifting time buffer and pound buffer.

* * * * *